United States Patent [19]

Shoemaker et al.

[11] Patent Number: 5,211,186
[45] Date of Patent: May 18, 1993

[54] PATIENT IMMOBILIZATION HARNESS AND APPARATUS

[76] Inventors: Michael D. Shoemaker, 206 S. Main, Mt. Vernon, Mo. 65712; Kenneth R. Foster, H.C.R. 6, Box 658, Reeds Spring, Mo. 65737

[21] Appl. No.: 791,914

[22] Filed: Nov. 13, 1991

[51] Int. Cl.$^5$ .................................. A61F 5/00
[52] U.S. Cl. .................................. 128/870; 128/369; 128/875
[58] Field of Search ............ 128/869, 870, 871, 875, 128/876, 87 B, 78; 602/5, 17, 18, 19, 20, 32

[56] References Cited

U.S. PATENT DOCUMENTS

| | | | |
|---|---|---|---|
| 1,561,399 | 11/1925 | Begg | 128/875 |
| 1,639,424 | 8/1927 | Breslin | 128/875 |
| 2,102,281 | 12/1937 | Pringle | 128/875 |
| 3,620,211 | 11/1971 | Goodell | 128/78 |
| 3,889,668 | 6/1975 | Ochs et al. | 128/870 |
| 3,933,154 | 1/1976 | Cabansag | 128/870 |
| 4,034,748 | 7/1977 | Winner | 128/870 X |
| 4,205,670 | 6/1980 | Owens | 128/875 |
| 4,422,454 | 12/1985 | English | 5/82 R |
| 4,515,155 | 5/1985 | Wagemann | 128/876 |
| 4,569,095 | 2/1986 | Holling | 128/876 X |
| 4,841,961 | 6/1989 | Binlage et al. | 128/876 |
| 4,911,105 | 3/1990 | Hocum | 128/875 |
| 5,014,374 | 5/1991 | Williams | 128/870 X |
| 5,016,620 | 5/1991 | Mathews | 128/870 X |
| 5,027,833 | 7/1991 | Calkin | 128/869 X |
| 5,031,639 | 7/1991 | Wolfer | 128/869 X |

Primary Examiner—Robert A. Hafer
Assistant Examiner—Sam Rimell

[57] ABSTRACT

A harness and backboard are provided for immobilizing an injured patient. The harness includes a medial strap which is adjustable in length so that laterally extending straps which are connected to the medial strap may be placed at the desired longitudinal positions on the patient. The lowermost lateral straps are of a length to permit them to be wrapped around the ankles and feet of the patient in a manner to support the patient when the backboard is tilted toward the feet. The straps include hook and loop type fastening means that allow the harness to be readily adapted to immobilize small children or large adults.

11 Claims, 3 Drawing Sheets

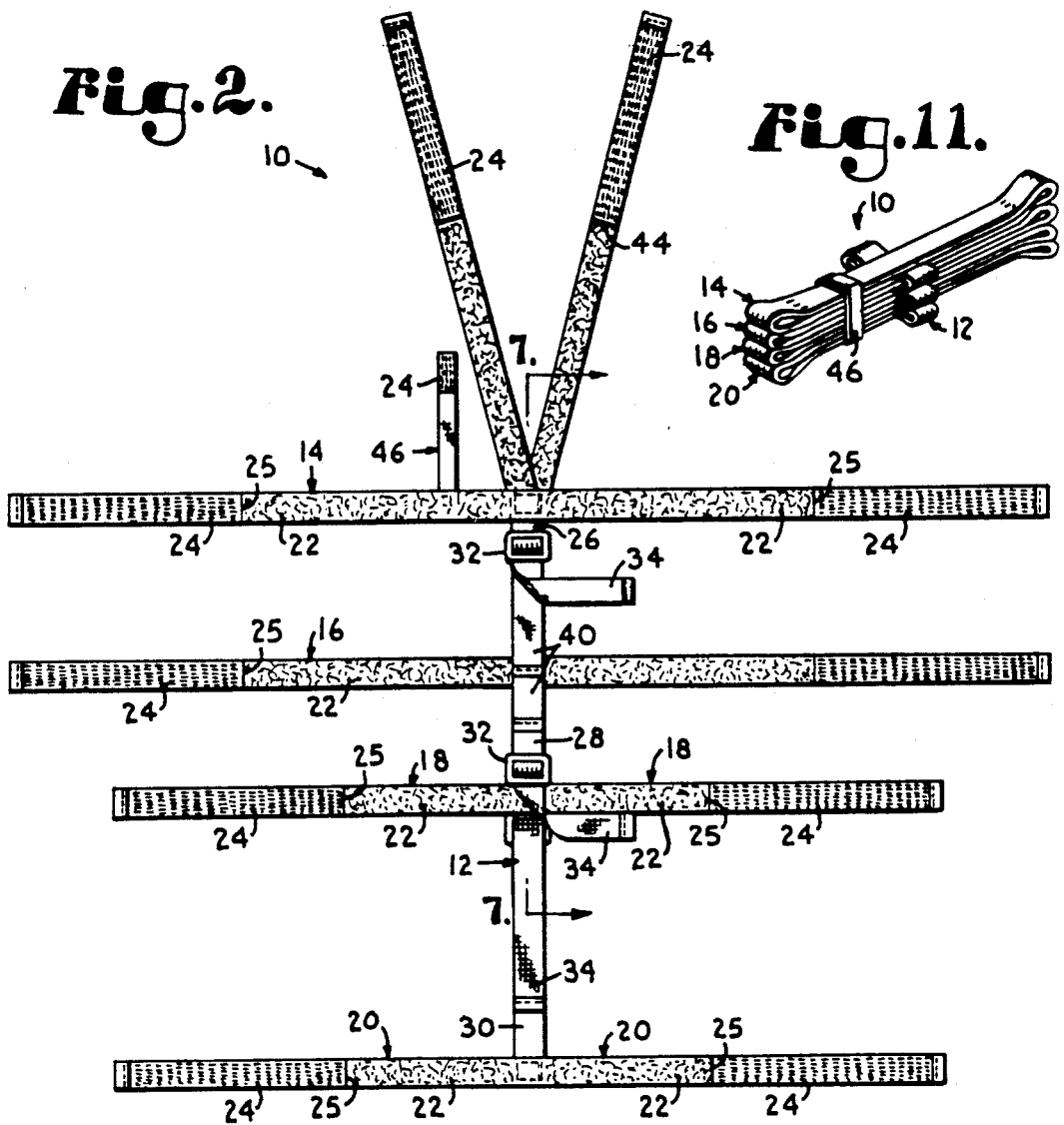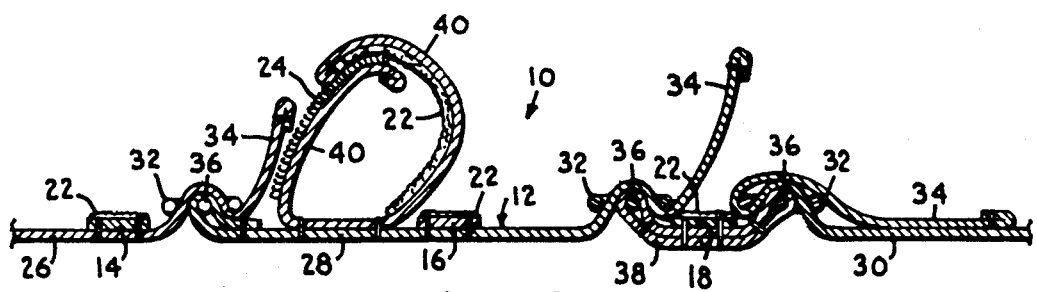

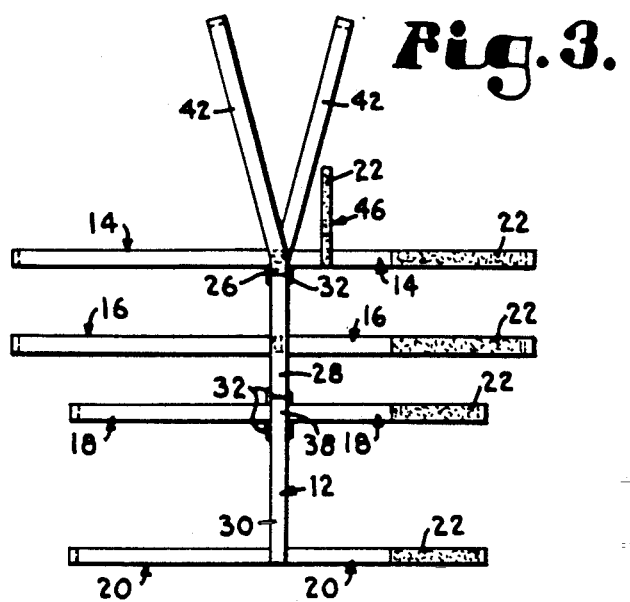
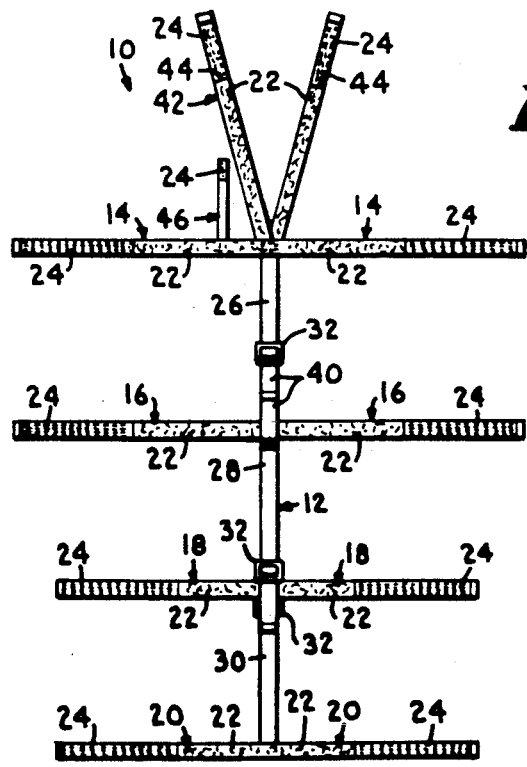
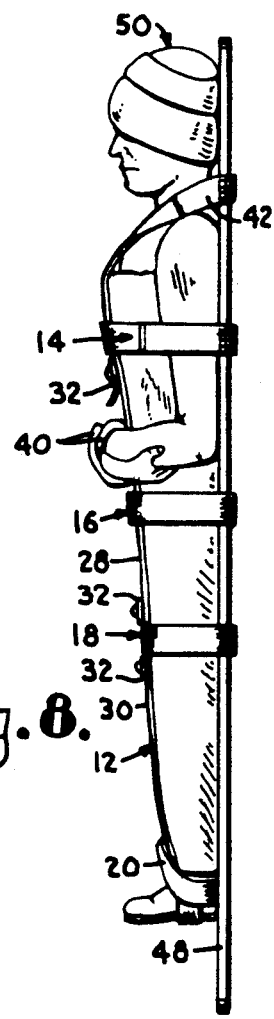
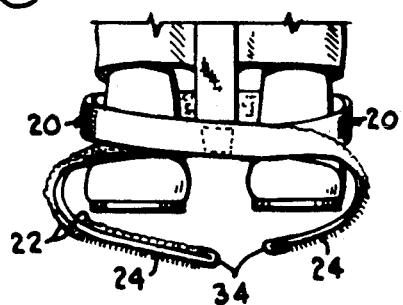
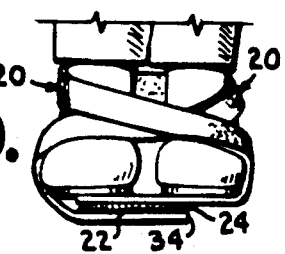

PATIENT IMMOBILIZATION HARNESS AND APPARATUS

BACKGROUND OF THE INVENTION

This invention relates generally to a patient immobilization harness and, more particularly, to an adjustable harness for immobilizing a patient on a support such as a backboard.

Restraint devices are commonly employed to immobilize an injured person who has suffered a possible spinal trauma so that the person can be transported to a hospital or other treatment facility. Because even the slightest movement of the injured spine may aggravate the neural damage to an extent that serious permanent disability may result, much attention has been focused on harness type restraint devices which are used in conjunction with a rigid or semi-rigid backboard to immobilize the spinal column and minimize the risk of further injury. Examples of such harnesses are provided in U.S. Pat. Nos. 3,889,668 to Ochs et al., 4,422,454 to English, and 4,841,961 to Burlage et al.

When restraining a patient on a backboard such as disclosed in U.S. Pat. No. 4,841,961, it is important to prevent bending or twisting movement of the spinal column as could be caused by lateral sliding movement of the patient on the backboard. The laterally extending straps provided in the harness disclosed in that patent cooperate with openings provided in the backboard to restrain the injured person in either a prone or supine position on the rigid board and are effective to reduce bending or twisting of the spine by restricting lateral sliding.

During transport of the patient, it is also important to prevent any longitudinal movement of the patient on the supporting device to minimize the risk of further injury resulting from such movement. While conventional harnesses are generally effective to prevent rotative and lateral movement, many are ineffective to restrain longitudinal movement which might occur if the backboard is tilted toward the patient's head or feet.

It is also desirable that the straps from the harness be placed over bony portions of the patient rather than areas such as the tracheal region where pressure applied to the larynx might obstruct the breathing airway. In harnesses which permit longitudinal shifting of the patient, such pressure can result by shifting of the straps even if the harness straps are initially placed appropriately.

Another problem associated with conventional harnesses is the difficulty in adapting the harness for use on individuals of different heights and girth. As a result, an emergency vehicle must be provided with a range of harness sizes so that the appropriate size is always available for use. In addition to the added expense and storage problems resulting from stocking a number of such harnesses, delays often result when trying to locate and apply the appropriately sized harness.

SUMMARY OF THE INVENTION

It is an object of this invention to provide a harness for securing an injured patient to a support structure such as a backboard in a manner which prevents longitudinal movement of the patient and possible aggravation of the injury should the backboard be tilted from a horizontal position toward the patient's feet.

It is also an object of this invention to provide a harness which is constructed in a manner to restrain an injured patient on a support structure such as a backboard to prevent lateral or rotative movement of the patient and which also prevent longitudinal movement of the patient should the backboard be tilted toward the patient's head so that the risk of further injury as a result of such tilting is substantially eliminated.

It is another object of this invention to provide a harness for immobilizing a patient on a support structure, which harness is adjustable in longitudinal as well as lateral length so that the harness may be readily adapted for use with patients having a wide range of lengths and girths and still provide proper placement of the harness straps over the desired portions of the patient's body.

It is a further object of this invention to provide a patient restraining harness which is readily adjustable to place the various straps across the bony portions of the patient's body and which is configured to prevent longitudinal movement of the patient when restrained on a backboard so that the straps remain positioned along the bony portions and are not placed across regions such as the patient's trachea where injury can result from the pressure applied by the straps.

It is a still further object of this invention to provide a patient immobilization apparatus comprising a harness and a backboard which may be quickly and easily applied to immobilize the patient so that the patient may be transported with substantially reduced risk of longitudinal, lateral and rotative movement of the patient and possible injury resulting from such movement.

To accomplish these and other related objects of the invention, in one aspect the invention is directed to a harness constructed for immobilizing a patient on a backboard or other transportable support surface, said harness comprising:
 a medial strap;
 a plurality of laterally extending straps coupled with the medial strap at spaced apart positions along the longitudinal length of the medial strap;
 fasteners coupled with the laterally extending straps for releasably coupling said laterally extending straps with the backboard; and
 means coupled with the medial strap for adjusting the length of said medial strap to permit the spacing between at least some of said laterally extending straps along the longitudinal length of said medial strap to be varied.

In another aspect, the invention is related to the combination of the harness and a backboard having a plurality of strap receiving devices, which combination provides a patient immobilization apparatus.

BRIEF DESCRIPTION OF THE DRAWINGS

In the accompanying drawings which form a part of the specification and are to be read in conjunction therewith and in which like reference numerals are used to indicate like parts in the various views:

FIG. 2 is a top plan view of the harness in accordance with the present invention with the various straps shown unfolded and lying flat and the several straps comprising the medial strap adjusted so that the medial strap is at a desired length;

FIG. 3 is a bottom plan view of the harness shown on a reduced scale and showing the reverse side of the harness from that shown in FIG. 2;

FIG. 4 is a top plan view of the harness similar to the view shown in FIG. 2 but showing the reverse side of the harness and with the medial strap shown adjusted to a longer length;

FIG. 7 is a fragmentary side elevational view of the harness taken in vertical section along line 7—7 of FIG. 2 in the direction of the arrows;

FIG. 8 is a side elevational view of the patient restraint apparatus illustrating the ability of the harness to support the patient even when the board is tilted to an upright position;

FIG. 9 is a fragmentary plan view of a lower portion of the harness and patient and illustrating the manner in which the ankle straps are wrapped around the patient's ankles and feet prior to fastening of the straps;

FIG. 10 is a fragmentary plan view of a lower portion of the harness and patient similar to the view shown in FIG. 9 but with the ankle straps fastened together to support the patient and prevent movement thereof in a longitudinal direction; and FIG. 11 is a perspective view of the harness in its folded storage condition.

DESCRIPTION OF THE PREFERRED EMBODIMENT

Figure 1:
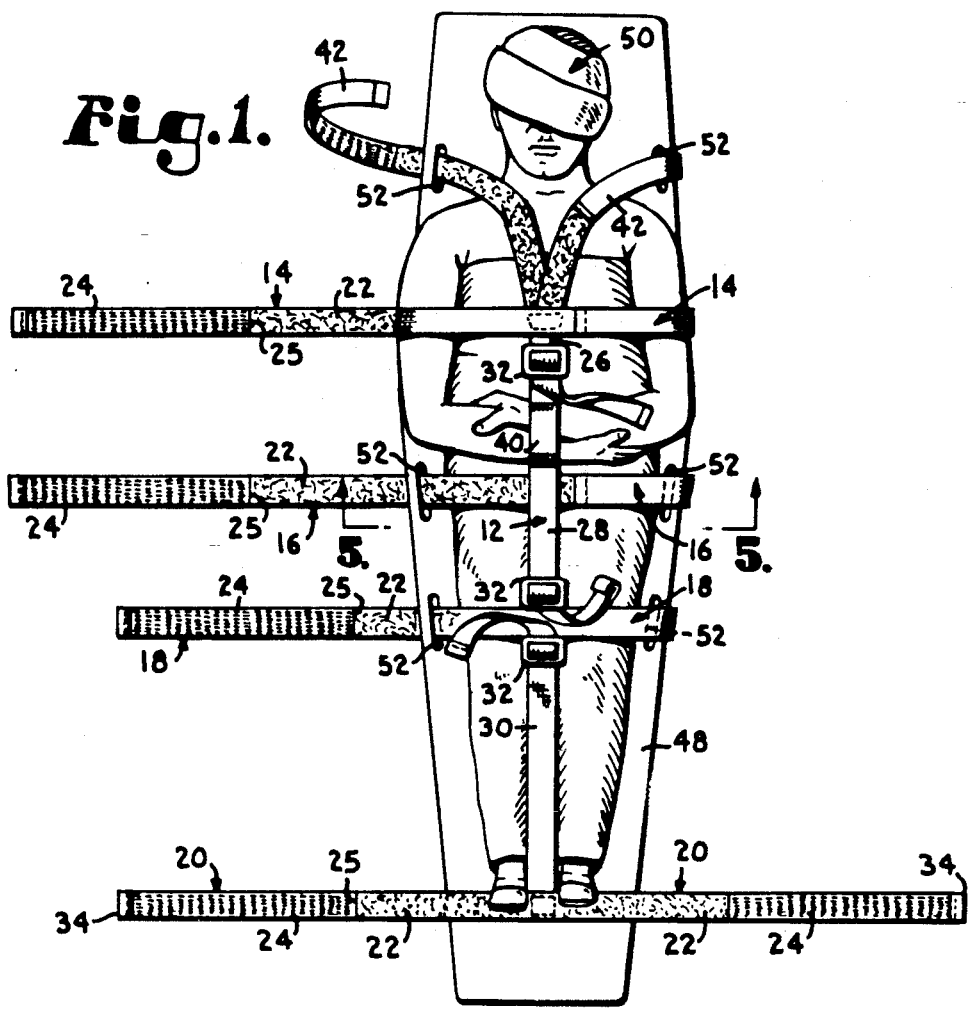
FIG. 1 is a top plan view of a patient immobilization apparatus in accordance with the present invention shown with a harness in the process of being applied to a backboard to immobilize the patient.

Referring now to the drawings in greater detail and initially to FIG. 2, a harness in accordance with the present invention is represented broadly by the numeral 10. Harness 10 is adapted to immobilize an injured patient on a support structure in a manner which will be subsequently described so that the patient may be transported to a treatment facility.

The harness 10 includes a medial strap 12 to which a plurality of pairs of laterally extending straps are attached. The pairs of straps include mid-sternum straps 14, hip straps 16 and mid-leg straps 18 which are spaced apart along the medial strap 12. The pairs of straps 14, 16 and 18 are preferably fixed to medial strap 12 in a permanent manner such as by sewing or other means. For purposes of strength, each pair of straps is also preferably formed as a single piece of material rather than two separate pieces joined at the medial strap 12.

The harness 10 further includes a pair of ankle straps 20 for wrapping around the patient's ankles and feet in a manner to support the patient when placed in an upright position. The ankle straps 20 are likewise preferably formed by a single length of material joined at its midpoint to the medial strap 12 in a permanent manner. The attachment of the ankle straps 20 to the medial strap 12 is at the lower end of the medial strap.

The length of the mid-sternum, hip, mid-leg and ankle straps 14, 16, 18 and 20 may be the same but need not be so. For example, because the girth around a patient's legs is typically less than that around the sternum and hips, the mid-leg straps 18 may be shorter than straps 14 and 16.

Each of straps 14, 16, 18 and 20 includes latching mechanisms in the form of lengths of interconnectable hook and loop type materials commonly available under the Velcro trademark. Each such strap includes a length of loop material 22 extending laterally from the medial strap 12 along the upper face of the strap. The end portion of each strap includes a length of hook material 24 which is also positioned on the upper face of the strap and abuts the loop material 22 at juncture 25. Substantially the entire upper face of each of straps 14, 16, 18 and 20 is thus covered by the lengths of loop and hook materials 22 and 24.

As can be seen in FIG. 3, the bottom face of one strap within each pair of straps 14, 16, 18 and 20 includes a length of loop material 22. The loop material 22 is position on the bottom face at the end portion of the associated strap in order to releasably interlock with the length of hook material 24 on the upper face of the other strap within each pair of straps to allow the straps to be pulled tightly around a person having a small girth.

Turning additionally to FIG. 2, it can be seen that the medial strap 12 comprises three shorter straps 26, 28 and 30 which are connected to slide buckles 32 in a manner that allows the effective length of each of those straps as well as the overall length of the medial strap 12 to be varied as desired. The coupling of those straps with buckles 32 is preferably accomplished in a manner to allow the effective length of each such strap to be shortened by simply pulling on a free end 34 of that strap. As can be seen in FIG. 7, this is achieved with respect to upper strap 26 by first looping the end opposite the free end 34 of middle strap 28 around a middle member 36 of buckle 32 and folding such end back onto the adjacent portion of the strap 28 and securing it thereto. The free end 34 of the upper strap 26 is then passed through the buckle 32 and around the middle member 36. The free end of the upper strap may then be folded back upon itself and sewn together to prevent the strap from thereafter being pulled completely through the buckle 32.

When coupled with the straps 26 and 28 in the described manner, the buckle 32 operates to permit the upper strap 26 to be pulled through the buckle by pulling on the free end 34 of the strap 26 to shorten the length of portion of the strap 26 contributing to the overall length of medial strap 12. When the strap 26 is pulled from its other end, the buckle bears against strap 26 to prevent movement in that direction. To lengthen the strap 26, the buckle may be simply tilted slightly to release the strap and the strap is pulled to achieve the length desired.

The coupling of lower and middle medial straps 30 and 28 with their respective buckles 32 can also be seen in FIG. 7. In order to connect those straps 30 and 28 with the buckles 32, the harness 10 includes another strap 38 which is coupled with the buckles 32 at positions adjacent both sides of the laterally extending mid-leg strap 18. Both ends of strap 38 are coupled with the middle member 36 of buckles 32 in the same manner as previously described with respect to the fastened end of middle strap 28. The free ends 34 of middle strap 28 and lower strap 30 are then passed through the buckles 32 and folded back upon and secured to themselves to prevent the straps from being pulled completely through the buckles 32.

The buckles 32 allow the effective length of the individual medial straps 26, 28 and 30 to be readily decreased by simply pulling on the free ends 34 of those straps. The length is likewise increased by pulling on the opposite ends of the straps while grasping the associated buckle 32 and tilting it slightly to release the strap. The laterally extending straps 14, 16 and 20 are connected respectively to the medial straps 26, 28 and 30, while laterally extending mid-leg strap 18 is secured to connecting strap 38. The longitudinal positioning of those lateral straps may thus be quickly varied to achieved the placement desired by simply adjusting the length of the medial straps 26, 28 and 30.

As best shown in FIG. 7, the harness 10 further includes a pair of arm restraint straps 40 which are attached to the upper face of the medial strap 12. The arm restraint straps are formed of a single length of material and are fixed to the middle medial strap 28 at a position between the laterally extending straps 14 and 16. One of arm restraint straps 40 includes a length of loop material 22 and the other strap 40 includes a cooperating length of hook material 24. The hook and loop materials 24 and 22 allow the straps 40 to be fastened together in a closed loop to secure the patient's arms in a position folded across the lower sternum.

Turning again to FIG. 2, the harness 10 additionally includes a pair of shoulder straps 42 which are coupled at one end to an upper end of the medial strap 12. The shoulder straps are preferable connected in a permanent manner to the end of the upper medial strap 26 at the same position that the laterally extending mid-sternum straps 14 are attached to the upper medial strap 26. The shoulder straps 42 extend obliquely to the line defined by the medial strap 12 and straps 42 preferably are oriented with respect to each other such that an acute angle is formed therebetween.

Both of the shoulder straps 42 include a length of loop material 22 connected to the upper face of the associated strap and extending from the fixed end toward the free end of the strap. The upper faces of the straps 42 also include a length of hook material 24 which extends from the free end toward the fixed end of the straps. The lengths of hook and loop material 24 and 22 abut at juncture 44 and cover substantially all of the upper face of both straps 42.

A storage strap 46 is connected to one of the mid-sternum straps 14 and, as shown in FIGS. 2-4, includes a length of hook material 24 on one face and a length of loop material 20 on the other face. As can be seen in FIG. 11, the harness can be folded up and secured by storage strap 46 by simply folding the laterally extending straps 14, 16, 18 and 20 and shoulder straps 42 inwardly and then stacking those straps on top of each other. The storage strap 46 is then secured about the stacked straps to retain the harness 10 in a compact condition for storage.

It will be appreciated that the material used to form the various straps of harness 10 should be flexible but should resist stretching. The material selected must also be sufficiently durable to withstand the rigors of usage, often in adverse weather conditions. Suitable materials are well known to those of skill in the art and include webbing material commonly used for seat belts in automobiles.

Turning additionally to FIGS. 1 and 8, the harness is used in conjunction with a suitable support such as a backboard 48 to provide an apparatus which immobilizes a patient 50 while permitting the patient to be transported to a treatment facility. It will be appreciated that other support devices such as ambulance cots, scoop stretchers, and stokes baskets may be used in place of the backboard 48.

Figure 5:
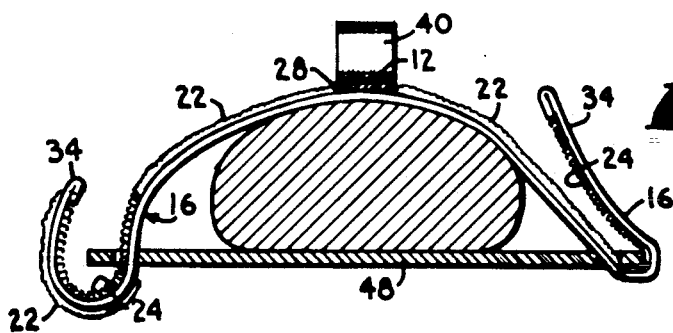
FIG. 5 is an elevational view of the patient immobilization apparatus taken in vertical section along line 5—5 of FIG. 1 in the direction of the arrows and shown on an enlarged scale and with the straps shown looped through apertures in the backboard and ready to be fastened.
Figure 6:
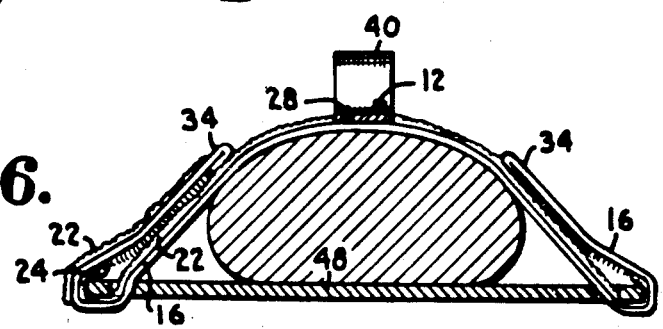
FIG. 6 is an elevational view of the patient immobilization apparatus similar to the view shown in FIG. 5 but with the straps shown in a fastened condition.

The backboard 48 is rigid and substantially planar and includes a plurality of strap receiving devices in the form of slots or apertures 52 formed along the lateral side edges of the board. As is best illustrated in FIG. 5 and 6, the free ends 34 of the various harness straps are passed through the apertures 52 and then looped around the edge of the board and fastened back upon the associated strap. Other devices such as brackets mounted on the board 48 may of course be used for this purpose in place of or in conjunction with apertures 52.

The apertures 52 are longitudinally positioned along the side edges of the backboard 48 at positions in alignment with the desired longitudinal placement of lateral straps 14, 16, 18 and 20 and shoulder straps 42. Additional apertures may also be provided along the side edges of the board 48 so that the backboard may be used with patients of different heights and still allow the lateral and shoulder straps to be placed at the desired positions on the patient.

In use, the harness 10 is unfurled from its folded storage position illustrated in FIG. 11 and applied on top of the patient 50 who has previously been placed in a supine or prone position on backboard 48. As shown in FIG. 1, the medial strap 12 is positioned to overlie the midline of the patient generally from the sternum to the feet. The harness is preferably positioned so that the mid-sternum straps 14 overlie the sternum of the patient 50 to secure the thoracic region. The individual straps 26, 28 and 30 of the medial strap 12 are then adjusted so that straps 16, 18 and 20 are positioned at the desired locations on the patient.

Each of laterally extending straps 14, 16 and 18 as well as shoulder straps 42 are then looped through the apertures 52 in backboard 48 and are then folded back upon themselves so that the lengths of loop and hook materials 22 and 24 interlock to fasten the straps.

As can been seen in FIGS. 8, 9 and 10, the ankle straps 20 are looped around the patient's ankles and feet in a manner to support the patient so that tilting of the patient towards the his feet does not result in longitudinal movement in that direction. In order to support the patient, the fixed ends of ankle straps 20 are placed adjacent the top surface of the board 48 and beneath the patient's feet. The straps are then wrapped laterally along the posterior and then forwardly along the lateral portion of the ankles. Each strap is then directed across the anterior portion of the ankle and across the top of the other foot before wrapping around the lateral side of that foot and then along the bottom of both feet. The interlocking of the loop and hook materials 22 and 24 on the respective straps 20 then secures the straps together. Any load then applied to those straps is then transfer to the medial strap 12 and distributed to the various lateral straps 14, 16 and 18 and shoulder straps 42 to support the load and prevent lateral movement of the patient in the direction of the patient's feet.

In order to prevent lateral movement in the direction of the patient's head it is important that the apertures 52 receiving the shoulder straps 42 be positioned closely to the patient's shoulders so that the straps 42 extend across the acromion processes or upper portions of the shoulders to prevent longitudinal movement of the patient in that direction.

The use of the pair of shoulder straps 42 extending obliquely to the line defined by the medial strap 12 and forming an acute angle is also particularly advantageous in that it allows the medial strap 12 to be terminated over the middle sternum portion of the patient. This insures that no portion of the shoulder straps 42 or medial strap 12 can overlie the patient's larynx where it might obstruct the patient's breathing.

The ability to adjust the length of medial strap 12 is particularly advantageous as it allows the laterally extending straps 14, 16, 18 and 20 to be placed at the appropriate positions on the patient 50. The straps can thus be placed over the desired bony portions of the patient's body by simply adjusting the length of the individual straps 26, 28 and 30 which comprise the medial strap 12. Notably, the use of a plurality of adjustable medial straps 26, 28 and 30 allows the laterally extending straps to be positioned generally independently of the placement of adjacent laterally extending straps. This allows the harness 10 to be used on patients having a wide range of heights while still allowing for proper placement of the straps.

It will also be appreciated that the laterally extending straps 14, 16, 18 and 20 as well as shoulder straps 42 may readily be adjusted to accommodate patients having a wide range of girths. As can be seen in FIG. 6, when the harness is used to immobilize an average-sized adult to backboard 48, the free ends 34 of hip straps 16 are spaced an appreciable distance from the medial strap 12 when the hip straps are folded back onto themselves and secured by the interlocking loop and hook materials 22 and 24. The provision of look and hook material along an entire face of each strap allows for a wide range of fastening positions to be achieved to accommodate larger and smaller sized individuals.

Of particular importance for securing a very small child or other individual having a small girth, one of the straps in each pair of lateral straps 14, 16, 18 and 20 may be extended to overlap onto the other strap in the pair with the loop and hook materials 22 and 24 interlocking to secure the overlapping strap onto the upper face of the other strap. The free end of the strap which has been overlapped may then be extended over the overlapping strap and secured to the loop material 22 provided on the other face of that strap. It is thus apparent that the provision of fastening material along the entire upper face faces of the straps as well as the use of fastening material along the other face of one of the straps permits the straps to securely and rapidly immobilize a patient onto the backboard 48 regardless of whether the individual is a small child or a large adult.

The provision of the arm restraining straps 40 on the medial strap 12 also facilitates immobilization of the patient's arms in a folded position across the lower sternum region of the patient. In certain applications, it may also be desirable to pass the mid-sternum straps 14 under the patient's arms rather than over them as illustrated in FIG. 1.

It can thus be seen that the harness 10 and backboard 48 cooperate to form a patient restraining apparatus which is readily adjustable to immobilize both children and adults so that they may be transported to a treatment facility in the immobilized conditioned. This greatly reduces the risk of further injury during transport of the patient such as when the patient has suffered a spinal injury and further movement of the spine could result in severe and permanent injury. The patient restraint apparatus formed by the harness 10 and backboard 48 also keeps the patient immobilized even if the backboard is tilted towards the patient's head or feet such as likely to occur if the individual is being transported over rough terrain from an accident site to an awaiting ambulance or helicopter.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. A harness constructed for immobilizing a patient on a backboard or other transportable support surface, said harness comprising:
   a medial strap comprising at least a first segment and a second segment coupled in longitudinal alignment;
   a plurality of laterally extending straps coupled with the medial strap at spaced apart positions along the longitudinal length of the medial strap, said plurality of laterally extending straps including a first lateral strap connected to said first segment of the medial strap and a second lateral strap connected to the second segment of the medial strap;
   fasteners coupled with the laterally extending straps for releasably coupling said laterally extending straps with the backboard; and
   a connector coupling the first and second segments of the medial strap, said connector permitting longitudinal movement of the first segment in relation to the second segment for adjusting the length of said medial strap and causing the spacing between the first and second lateral straps along the longitudinal length of said medial strap to be varied.

2. The harness of claim 1, including shoulder straps connected to the medial strap at one end thereof and extending obliquely to a line defined by said medial strap, and wherein an angle formed by said shoulder straps is an acute angle.

3. The harness of claim 1, including an auxiliary strap coupled with the medial strap and including fasteners for forming said auxiliary strap in a closed loop lying in a plane extending along the longitudinal length of the medial strap.

4. The harness of claim 1, wherein said plurality of laterally extending straps includes a plurality of straps extending substantially perpendicularly to the longitudinal length of the medial strap.

5. The harness of claim 4, wherein said medial strap includes a third segment in longitudinal alignment with said first and second segments and wherein said plurality of longitudinally extending straps includes a third lateral strap connected to said third segment, and including another connector coupling said second segment with the third segment to permit longitudinal movement of the third segment in relation to the second segment for adjusting the length of said medial strap and causing the spacing between said third and second lateral straps along the longitudinal length of the medial strap to be varied.

6. The harness of claim 5, wherein said fasteners comprise loop material on a portion of said laterally extending straps and hook material releasably interconnectable with said loop material on another portion of each of said laterally extending straps, whereby said laterally extending straps may be folded upon themselves to interconnect the hook material with the loop material.

7. The harness of claim 6, wherein said loop material and said hook material extend along a substantial portion of one face of some of said laterally extending straps.

8. The harness of claim 7, wherein said loop material and said hook material extend along substantially all of one face of some of said laterally extending straps.

9. The harness of claim 8, wherein at least a pair of said laterally extending straps are in alignment and extend in opposite lateral directions from a common portion along the length of the medial strap.

10. The harness of claim 9, including hook material and loop material along one face of both of said straps within said pair of laterally extending straps, and further including hook or loop material along an opposite face of one of said straps in said pairs of straps, whereby the other of said straps in said pair of strap may be releasably secured to said one strap by interconnecting said hook or loop material on said one face of one strap with the hook or loop material on said opposite face of the other strap.

11. The harness of claim 2, wherein said plurality of laterally extending straps includes a pair of straps connected to an end of the medial strap opposite from said one end at which the shoulder straps are connected to the medial strap and wherein said medial strap can be adjusted to a length wherein said pair of laterally extending straps may be wrapped around feet of said patient.

* * * * *